(12) United States Patent
Beyerlein

(10) Patent No.: US 7,364,567 B2
(45) Date of Patent: Apr. 29, 2008

(54) SYSTEMS AND METHODS FOR DETECTING TISSUE CONTACT AND NEEDLE PENETRATION DEPTH

(75) Inventor: Dagmar Beyerlein, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 326 days.

(21) Appl. No.: 10/166,854

(22) Filed: Jun. 10, 2002

(65) Prior Publication Data

US 2005/0004513 A1  Jan. 6, 2005

(51) Int. Cl.
*A61M 5/00* (2006.01)

(52) U.S. Cl. .................................................. 604/117
(58) Field of Classification Search ........ 604/116–118, 604/131, 264, 272, 505, 246, 275, 66; 600/104, 600/117, 202, 424, 485–488, 550, 561; 606/167, 606/170, 172
See application file for complete search history.

(56) References Cited

U.S. PATENT DOCUMENTS

| | | | | |
|---|---|---|---|---|
| 2,001,638 | A | * | 5/1935 | Tornsjo ................ 604/165.02 |
| 4,186,750 | A | * | 2/1980 | Patel ........................ 600/561 |
| 4,299,230 | A | * | 11/1981 | Kubota ..................... 600/300 |
| 4,356,826 | A | * | 11/1982 | Kubota ..................... 600/300 |
| 4,964,854 | A | | 10/1990 | Luther |
| 5,279,567 | A | * | 1/1994 | Ciaglia et al. ............. 604/117 |
| 5,292,309 | A | * | 3/1994 | Van Tassel et al. ........ 604/117 |
| 5,396,897 | A | * | 3/1995 | Jain et al. .................. 600/561 |
| 5,419,777 | A | | 5/1995 | Hofling |
| 5,421,821 | A | * | 6/1995 | Janicki et al. ............... 604/26 |
| 5,425,376 | A | | 6/1995 | Banys et al. |
| 5,454,791 | A | * | 10/1995 | Tovey et al. .............. 604/118 |
| 5,470,316 | A | * | 11/1995 | Tovey et al. .............. 604/118 |

(Continued)

FOREIGN PATENT DOCUMENTS

DE    44 20 232 A1   12/1995

OTHER PUBLICATIONS

PCT Search Report dated Dec. 16, 2004, 8 pages.

(Continued)

*Primary Examiner*—Kevin C. Sirmons
*Assistant Examiner*—Catherine N. Witczak
(74) *Attorney, Agent, or Firm*—Blakely, Sokoloff, Taylor & Zafman LLP

(57) ABSTRACT

Systems and methods for determining tissue contact and penetration depth are provided. In one aspect, the system includes a needle and a pressure measurement assembly. The needle, in one exemplary embodiment, includes a first end and a second end with at least one aperture located a predetermined distance from the first end. The pressure measurement assembly is connected with a portion of the needle to measure pressure of fluid flowing through the needle. The pressure measurement assembly measures a first pressure when the needle contacts tissue and a second difference in pressure when the needle penetrates the tissue and the aperture becomes occluded.

In an alternative aspect, the system includes a needle and a sensor. The sensor, in another exemplary embodiment, is coupled with a portion of the needle to detect tissue contact pressure on the sensor as the needle penetrates tissue and makes contact with the sensor. The sensor is located a predetermined distance from the first end of the needle.

4 Claims, 13 Drawing Sheets

U.S. PATENT DOCUMENTS

| | | | |
|---|---|---|---|
| 5,496,273 | A | 3/1996 | Pastrone et al. |
| 5,551,427 | A | 9/1996 | Altman |
| 5,571,133 | A * | 11/1996 | Yoon ........................... 606/185 |
| 5,649,911 | A * | 7/1997 | Trerotola ............... 604/164.01 |
| 5,656,339 | A | 8/1997 | Wesseling et al. |
| 5,662,107 | A * | 9/1997 | Sakariassen ................ 600/369 |
| 5,746,713 | A | 5/1998 | Hood et al. |
| 5,800,395 | A * | 9/1998 | Botich et al. ............... 604/110 |
| 5,817,074 | A * | 10/1998 | Racz ........................... 604/272 |
| 5,871,495 | A | 2/1999 | Mueller |
| 5,873,366 | A | 2/1999 | Chim et al. |
| 5,878,751 | A | 3/1999 | Hussei et al. |
| 5,928,943 | A | 7/1999 | Franz et al. |
| 5,941,868 | A | 8/1999 | Kaplan et al. |
| 5,954,701 | A * | 9/1999 | Matalon ..................... 604/272 |
| 5,964,757 | A | 10/1999 | Ponzi |
| 6,030,377 | A | 2/2000 | Linhares et al. |
| 6,102,887 | A | 8/2000 | Altman et al. |
| 6,102,926 | A | 8/2000 | Tartaglia et al. |
| 6,162,202 | A * | 12/2000 | Sicurelli et al. ............ 604/272 |
| 6,217,554 | B1 | 4/2001 | Green |
| 6,251,079 | B1 | 6/2001 | Gambale et al. |
| 6,254,573 | B1 | 7/2001 | Haim et al. |
| 6,283,951 | B1 | 9/2001 | Flaherty et al. |
| 6,302,870 | B1 | 10/2001 | Jacobsen et al. |
| 6,309,370 | B1 | 10/2001 | Haim et al. |
| 6,391,005 | B1 | 5/2002 | Lum et al. |
| 6,494,862 | B1 | 12/2002 | Ray et al. |
| 6,517,521 | B1 * | 2/2003 | Ly ............................. 604/239 |
| 6,546,787 | B1 | 4/2003 | Schiller et al. |
| 6,620,139 | B1 | 9/2003 | Plicchi et al. |
| 6,905,476 | B2 | 6/2005 | Ponzi |
| 7,094,201 | B1 | 8/2006 | Stokes et al. |
| 2003/0083686 | A1 | 5/2003 | Freeman et al. |
| 2004/0092893 | A1* | 5/2004 | Haider et al. ............... 604/272 |
| 2004/0171933 | A1 | 9/2004 | Stoller et al. |
| 2005/0027199 | A1 | 2/2005 | Clarke |

OTHER PUBLICATIONS

Chapter 1 PCT International Preliminary Report (IPER) for PCT Application No. PCT/US2004/027961. Mailed on Mar. 16, 2006 (9 pages).

* cited by examiner

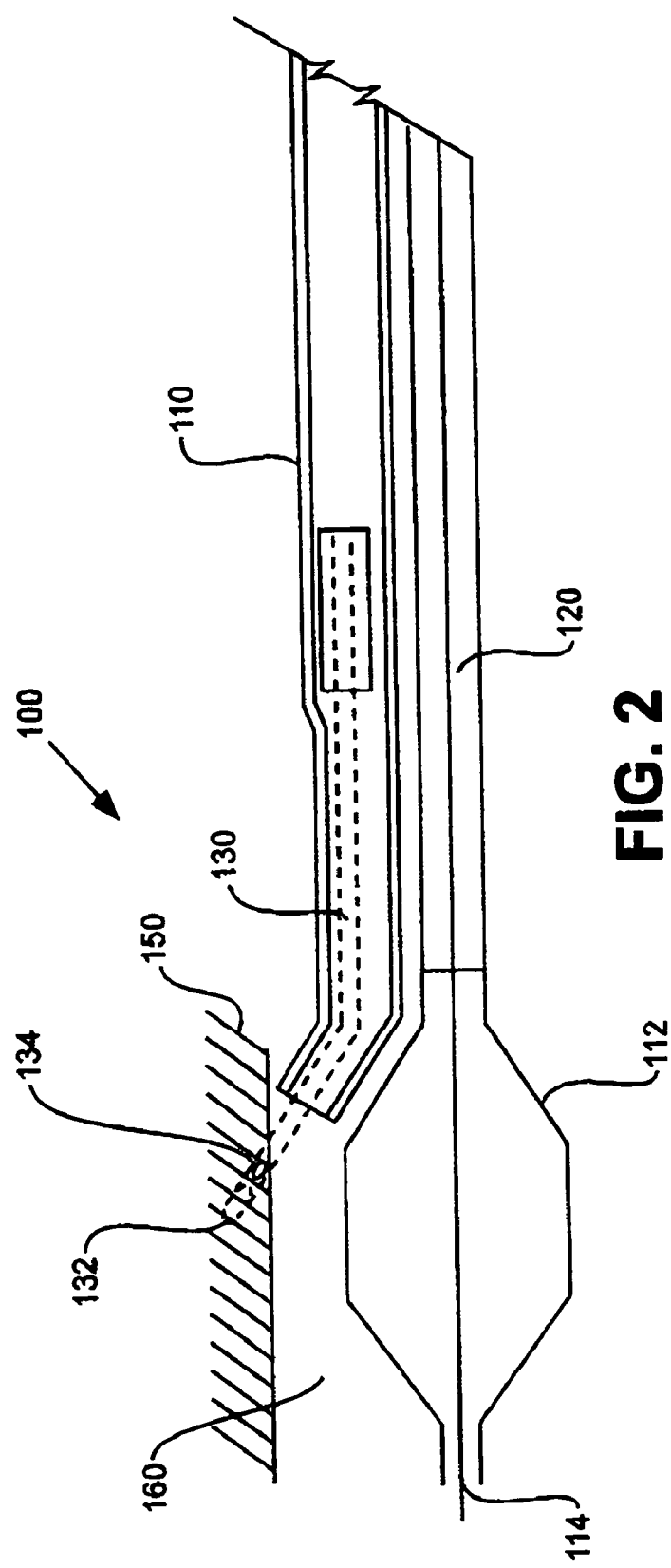

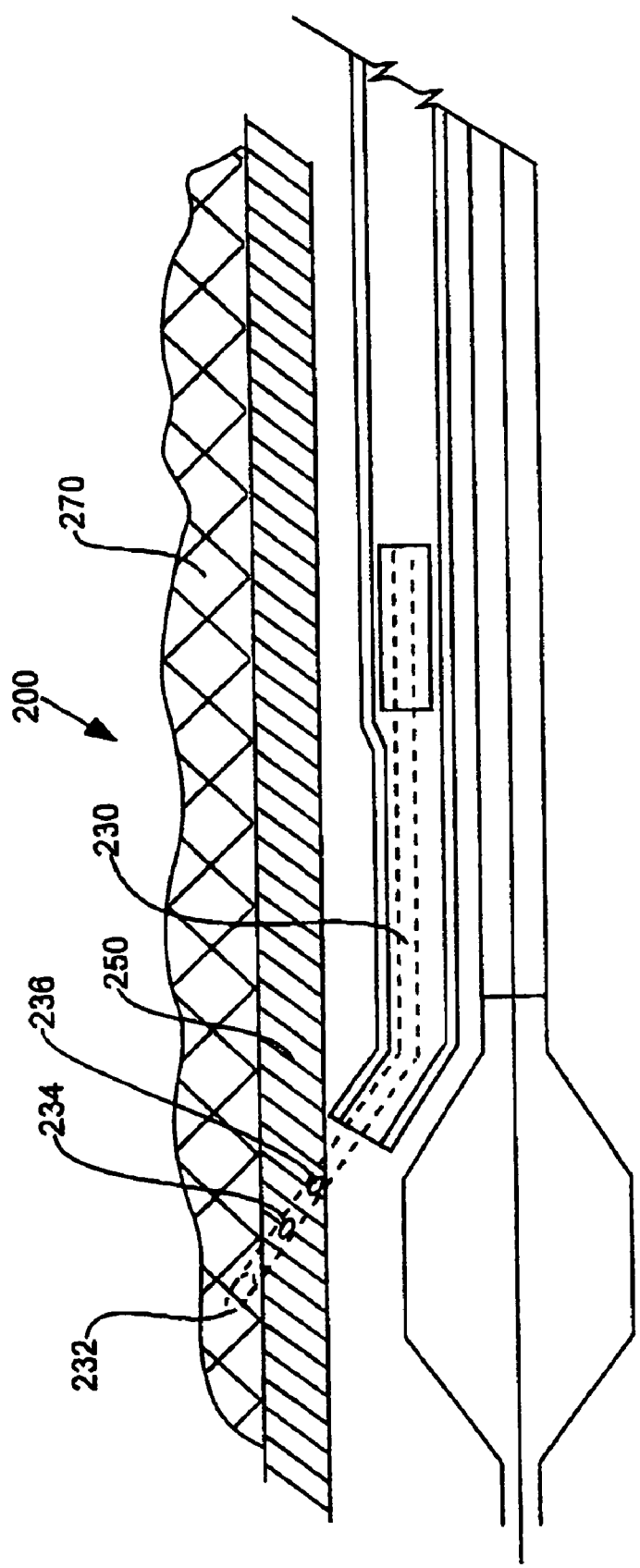

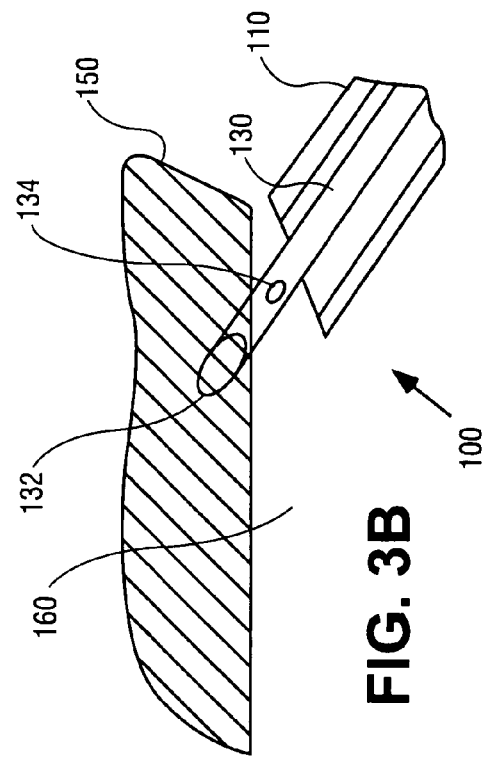
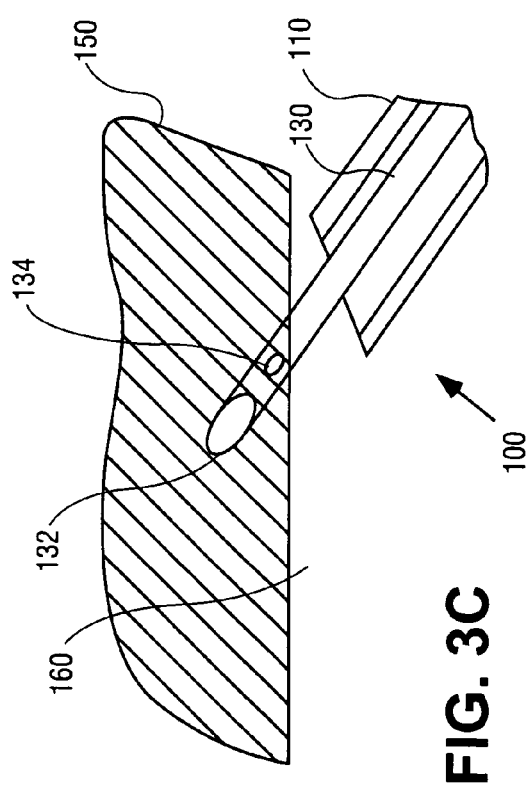
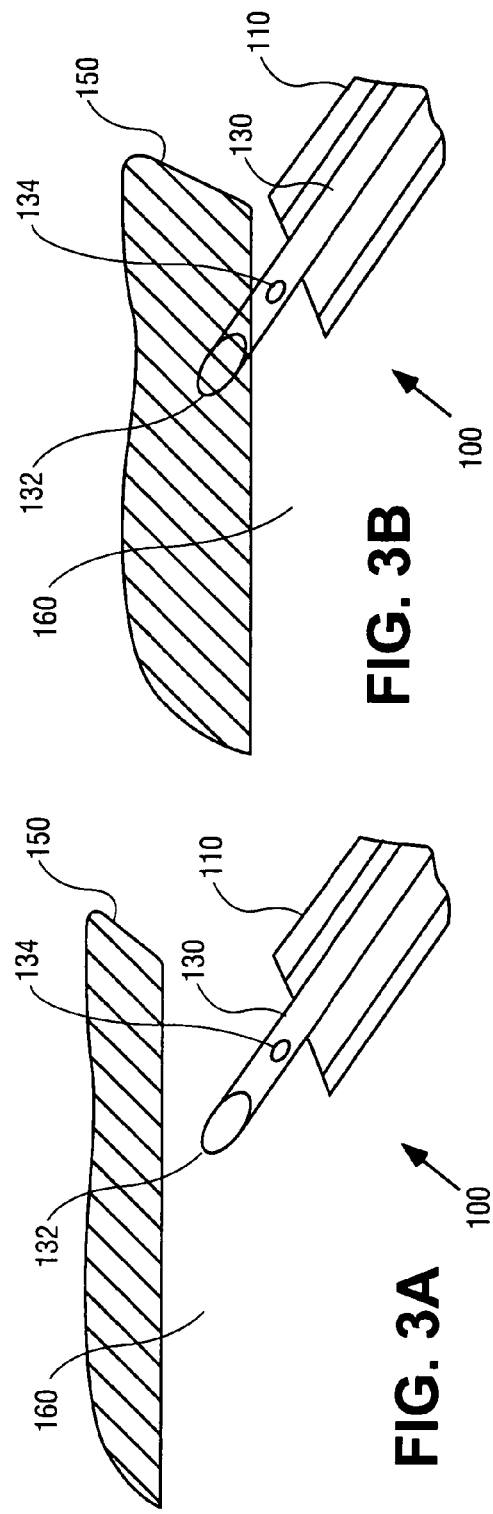

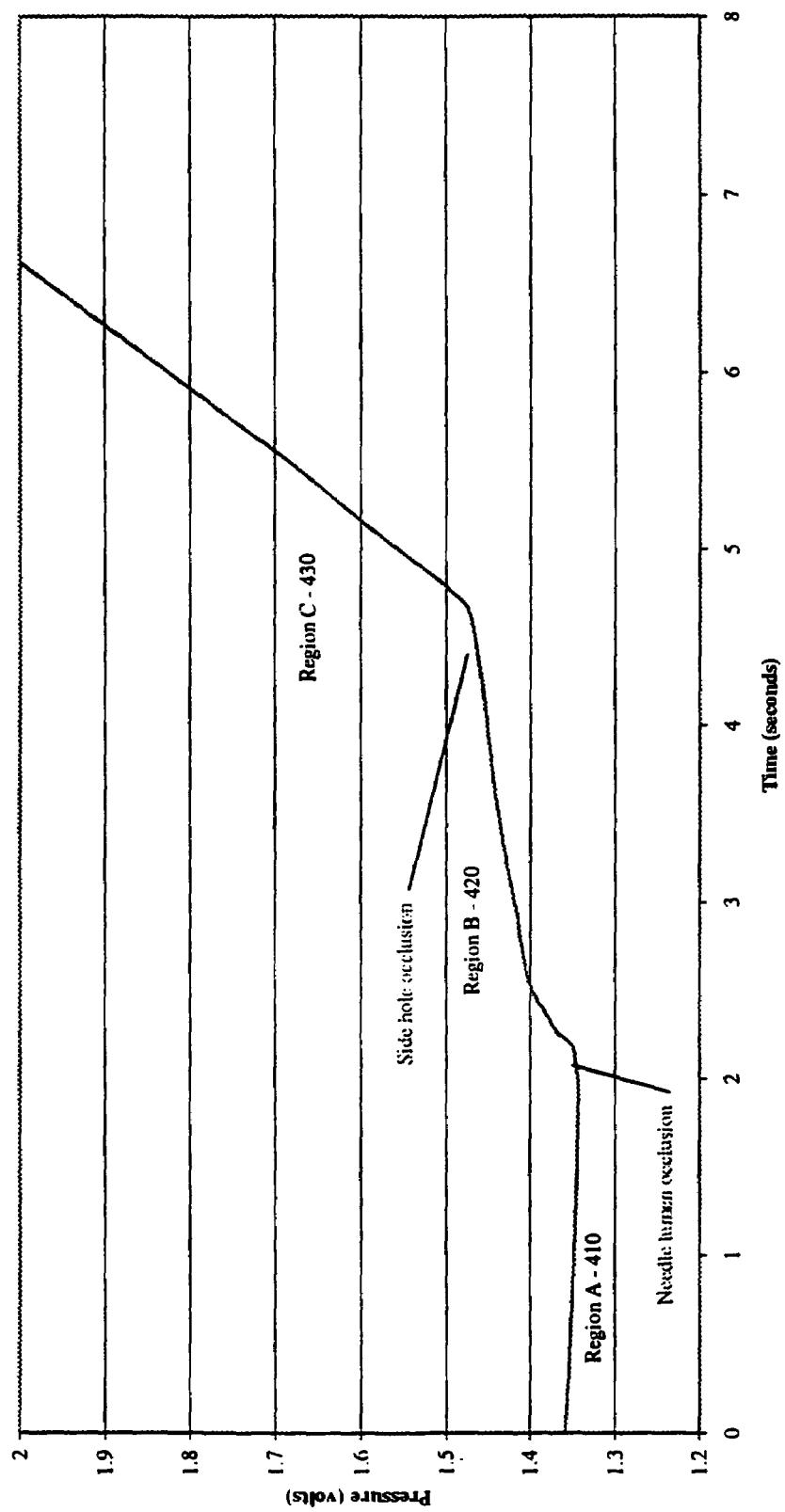

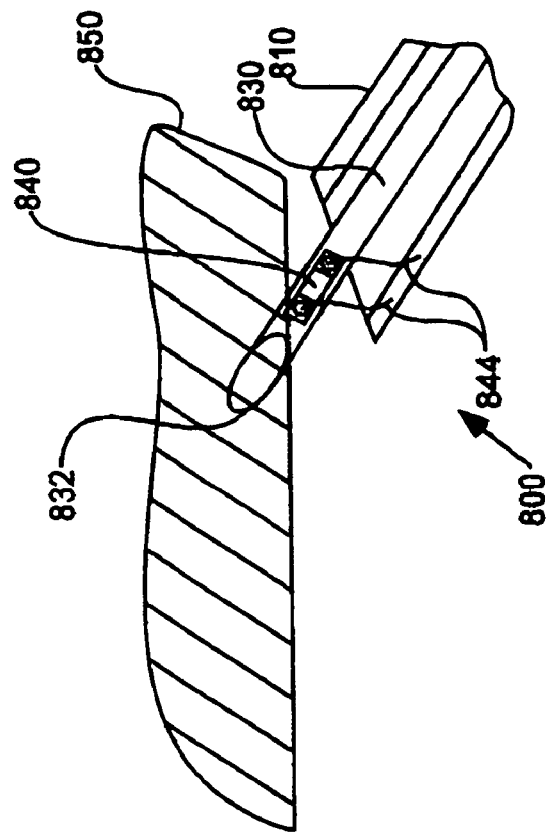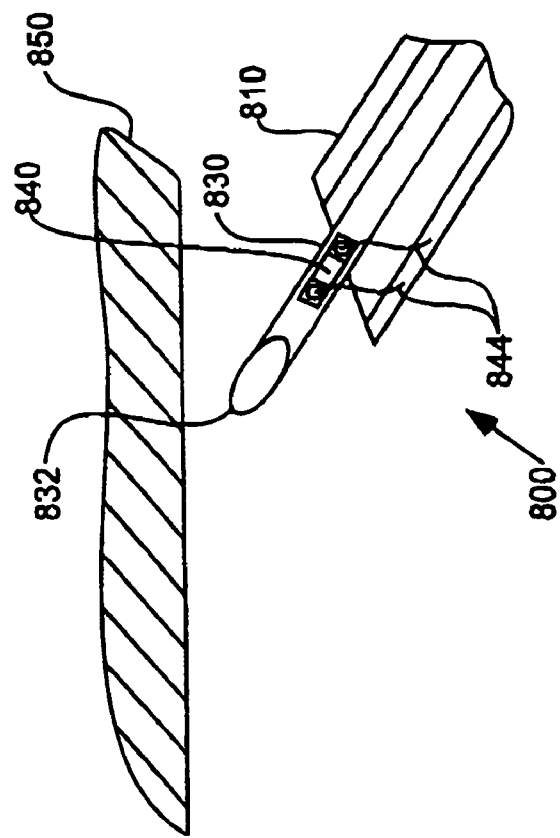
FIG. 7A
FIG. 7B

SYSTEMS AND METHODS FOR DETECTING TISSUE CONTACT AND NEEDLE PENETRATION DEPTH

FIELD OF THE INVENTION

The invention relates generally to needles, and more particularly, to a system and method for detecting tissue contact and needle penetration depth.

BACKGROUND

Drug delivery systems currently exist that supply therapeutic substances through a needle to regions of a patient's body. Such regions may include a diseased blood vessel, body cavity or organ. In the case of a diseased blood vessel, for example, the therapeutic agent may be used to treat an arterial lesion and/or to promote an angiogenic response In some applications, a needle may be connected to a catheter assembly to deliver the therapeutic agent deep into the body. In this application, it is often difficult to determine when the needle contacts the organ, cavity wall, or vessel wall. Further, it is difficult to determine the penetration depth of the needle. In many of the applications for which a needle catheter assembly is used to deliver therapeutic agents to regions within the body, the agent must be delivered to a precise location. Accordingly, it is desirable to provide feedback that indicates when the needle contacts the cavity or vessel wall and when the needle has been inserted to a predetermined depth.

SUMMARY OF THE INVENTION

Systems and methods for determining tissue contact and penetration depth are provided. In one aspect, the system includes a needle and a pressure measurement assembly. The needle, in one exemplary embodiment, includes a first end and a second end with at least one aperture located a predetermined distance from the first end. The pressure measurement assembly is connected with a portion of the needle to measure pressure of fluid flowing through the needle. The pressure measurement assembly measures a first pressure when the needle contacts tissue and a second difference in pressure when the needle penetrates the tissue and the aperture becomes occluded.

In an alternative aspect, the system includes a needle and a sensor. The sensor, in another exemplary embodiment, is coupled with a portion of the needle to detect tissue contact pressure on the sensor as the needle penetrates tissue and makes contact with the sensor. The sensor is located a predetermined distance from the first end of the needle.

BRIEF DESCRIPTION OF THE DRAWINGS

The present invention is illustrated by way of example, and not limitation, in the figures of the accompanying drawings in which:

FIG. 2 illustrates the embodiment of the fluid delivery catheter of FIG. 1 where the needle penetrates tissue;

FIG. 2a illustrates an alternative embodiment of a fluid delivery catheter where a needle penetrates and extends into tissue beyond the vessel wall;

FIGS. 3a-3c illustrate the embodiment of the fluid delivery catheter of FIG. 1 in different positions with respect to the tissue;

FIG. 4 illustrates a graph representing different fluid injection pressure measurements within the needle corresponding to various positions of the needle with respect to the tissue as shown in FIGS. 3a-3c;

FIGS. 7a and 7b illustrate the embodiment of the fluid delivery catheter of FIG. 7 in different positions with respect to the tissue;

DETAILED DESCRIPTION

Systems and methods for detecting tissue contact and needle penetration depth are described. In the following detailed description of the present invention, numerous specific details are set forth in order to provide a thorough understanding of the present invention. However, it will be apparent to one skilled in the art that the present invention may be practiced without these specific details. In some instances, well-known structures and devices are shown in block diagram form, rather than in detail, in order to avoid obscuring the present invention. Several exemplary embodiments are described herein, and it will be appreciated that alternative embodiments exist within the scope of this invention.

Figure 1:
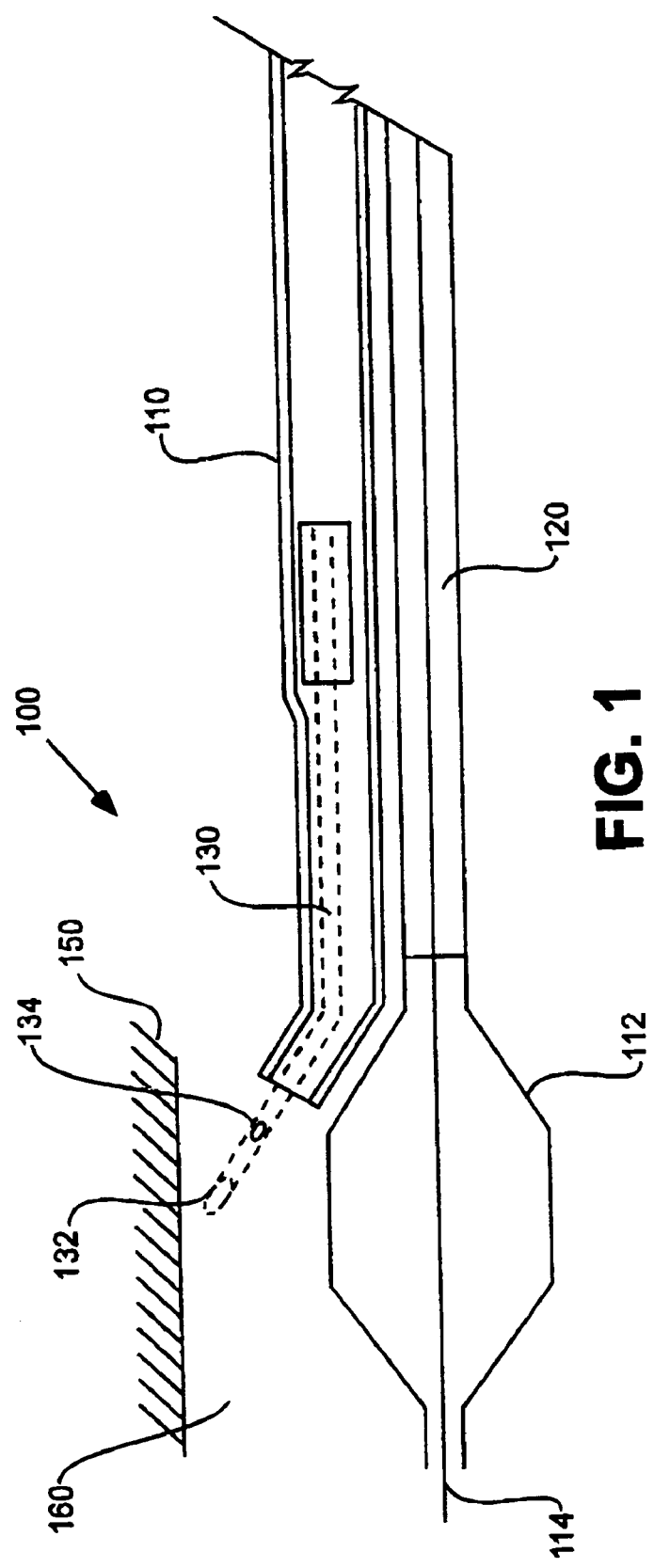
FIG. 1 illustrates a side cross-sectional view of one embodiment of a fluid delivery catheter.

FIG. 1 illustrates a side cross sectional view of one embodiment of a fluid delivery catheter 100. The fluid delivery catheter 100 can be used to provide therapeutic agents to a particular region of a patient's body, for example, to prevent or treat arterial disease (e.g. arterial stenosis or restenosis). The fluid delivery catheter 100 can be any medical device designed for insertion into a region of a patient's body to permit injection of fluids. It is contemplated that the fluid delivery catheter has applicability for use with any region within a patient's body, including blood vessels (e.g. coronary arteries), urinary tract, intestinal tract, kidney ducts, and the like.

In FIG. 1, the fluid delivery catheter 100 includes a needle 130 within a needle sheath 110. The needle sheath is mounted on a dilatation catheter 120. The fluid delivery catheter 100 is shown within a cavity 160 of a patient's body in FIG. 1. The cavity 160 may be a lumen of a blood vessel, such as a coronary artery. The fluid delivery catheter 100 is maneuvered over a guidewire 114. The guidewire directs the fluid delivery catheter 100 through torturous passageways within the body to arrive at the desired body cavity 160. The dilatation catheter 120 has a balloon 112 that inflates and directs the needle tip 132, which is extendable, toward body tissue such as a blood vessel wall 150.

The needle 130 includes a needle tip 132 and an aperture 134 located a predetermined distance from the needle tip 132. As the needle 130 is inserted into body tissue, first the needle tip 132 and then the aperture 134 become occluded. This is shown in FIG. 2. The occlusion of the needle tip 132 and aperture 134 increase the injection pressure of the fluid within the needle 130, thereby allowing an operator to determine tissue contact and penetration depth of the needle 130.

In one embodiment the needle 130 may include more than one aperture 134 spaced in predetermined measurements from the needle tip 132 of the needle 130. For example, a first aperture 134 may be located a first predetermined distance from the needle tip 132. A second aperture (not shown) may be located a second predetermined distance from the first aperture 134. In alternative embodiments, there may be more than two apertures.

In one embodiment, the space between the apertures may be the same. In other alternative embodiments, the distances between the apertures may be different. In another embodiment, the apertures may all be the same size and shape while in another embodiment the sizes and shapes of the apertures could be different. The apertures should be much smaller than the needle tip 132 lumen so that the fluid will be ejected from the needle tip 132 rather than the aperture 134. The occlusion of both the needle tip 132 and individual aperture 134 and the concomitant increases of injection pressure allow an operator to determine the penetration depth of the needle 130 as it becomes embedded in the vessel wall 150.

FIG. 2 illustrates the embodiment of the fluid delivery catheter 100 of FIG. 1 where the needle 130 is shown penetrating a vessel wall 150. As the needle tip 132 contacts the vessel wall 150, the needle tip 132 becomes occluded. Then, as the needle 130 further penetrates the vessel wall 150, the aperture 134 that is located a predetermined distance from the needle tip 132 becomes occluded. Accordingly, in alternative embodiments, the predetermined distance between the needle tip 132 and aperture 134 may vary according to what the desired penetration depth may be.

In one embodiment, injection pressure measurements are taken continuously as a therapeutic agent is injected from the first end of a needle, through the needle 130, and to the needle tip 132.

As the vessel wall or other tissue within the body occludes the needle tip 132, an increase in pressure will occur. Accordingly, an operator is able to determine by the increase in fluid pressure that the needle tip 132 has contacted the vessel wall. As the vessel wall or other tissue occludes the aperture 134, another increase in fluid pressure will occur. An operator is again able to determine by the second increase in pressure that the needle 130 has been inserted to a predetermined depth in the tissue or vessel wall 150.

FIG. 2a illustrates an alternative embodiment of a fluid delivery catheter 200 where a needle 230 penetrates and extends into tissue 270 beyond the vessel wall 250. In FIG. 2a, the needle 230 includes more than one aperture. The first aperture 234 is located a predetermined distance from the needle tip 232 so that occlusion of the first aperture 234 indicates penetration of the needle 230 a certain depth into the first tissue layer or vessel wall 250. The second aperture 236 is located a predetermined distance from the first aperture 234 so that the occlusion of the second aperture 236 indicates a further penetration of the needle 230. In some cases, an operator may have knowledge about the thickness of certain tissue. For example, the vessel wall 250 may be a known thickness. The second aperture 236 may then be placed according to that known thickness so that occlusion of the second aperture 236 indicates the needle 230 has penetrated all the way through the first layer of tissue 250 and into the second layer of tissue 270.

FIGS. 3a-3c illustrate the embodiment of the fluid delivery catheter 100 in different positions with respect to the vessel wall 150. FIG. 3a illustrates the fluid delivery catheter 100 where the needle 130 has not yet contacted the vessel wall 150. The needle tip 132 is close to and proximate to but not contacting the vessel wall 150.

FIG. 3b illustrates the fluid delivery catheter 100 where a portion of the needle tip 132 is contacting and has become embedded in the vessel wall 150. However, the needle 130 has not been fully inserted into the vessel 150. Accordingly, as seen in FIG. 3b, the desired penetration depth of the needle 130 has not been achieved.

FIG. 3c illustrates the fluid delivery catheter 100 where the needle 130 has penetrated the vessel wall 150 to a predetermined depth. The desired penetration depth has been achieved when the vessel wall 150 occludes the aperture 134. As seen in FIG. 3c, both the needle tip 132 and the aperture 134 are embedded within the vessel wall 150. Accordingly, as discussed above, an operator is able to determine by the increase in injection pressure caused by the occlusion of the aperture 134 that the needle 130 has penetrated tissue to a predetermined depth.

FIG. 4 illustrates a graph representing different pressure measurements of fluid within the needle 130 taken at the three needle positions shown in FIGS. 3a through 3c. The graph is representative of pressure versus time where it is assumed that the needle 130 is pushed into vessel wall 150 over time in the sequence shown in FIGS. 3a (first), 3b (next), and 3c (last). As the needle 130 is in the body cavity 160 as seen in FIG. 3a but not contacting the vessel wall 150, the injection pressure is lower than the scenarios shown in FIGS. 3b and 3c. This pressure measurement is shown as region A 410 in FIG. 4. As a portion of the needle tip 132 penetrates the vessel wall 150, an increase in pressure occurs. The pressure increases dramatically after the needle tip lumen 132 becomes occluded, but the rate decreases slightly shortly thereafter as shown in region B 420 in FIG. 4. As the needle 130 penetrates the tissue or the vessel wall 150 a predetermined depth and the aperture 134 becomes occluded, a second dramatic increase in pressure is detected. This pressure spike is shown as region C 430 in FIG. 4. Although only 3 points are shown in FIG. 4 corresponding to FIGS. 3a 3b and 3c, if additional apertures were to be added on the needle, additional pressure increases would occur as each aperture became occluded.

Figure 5:
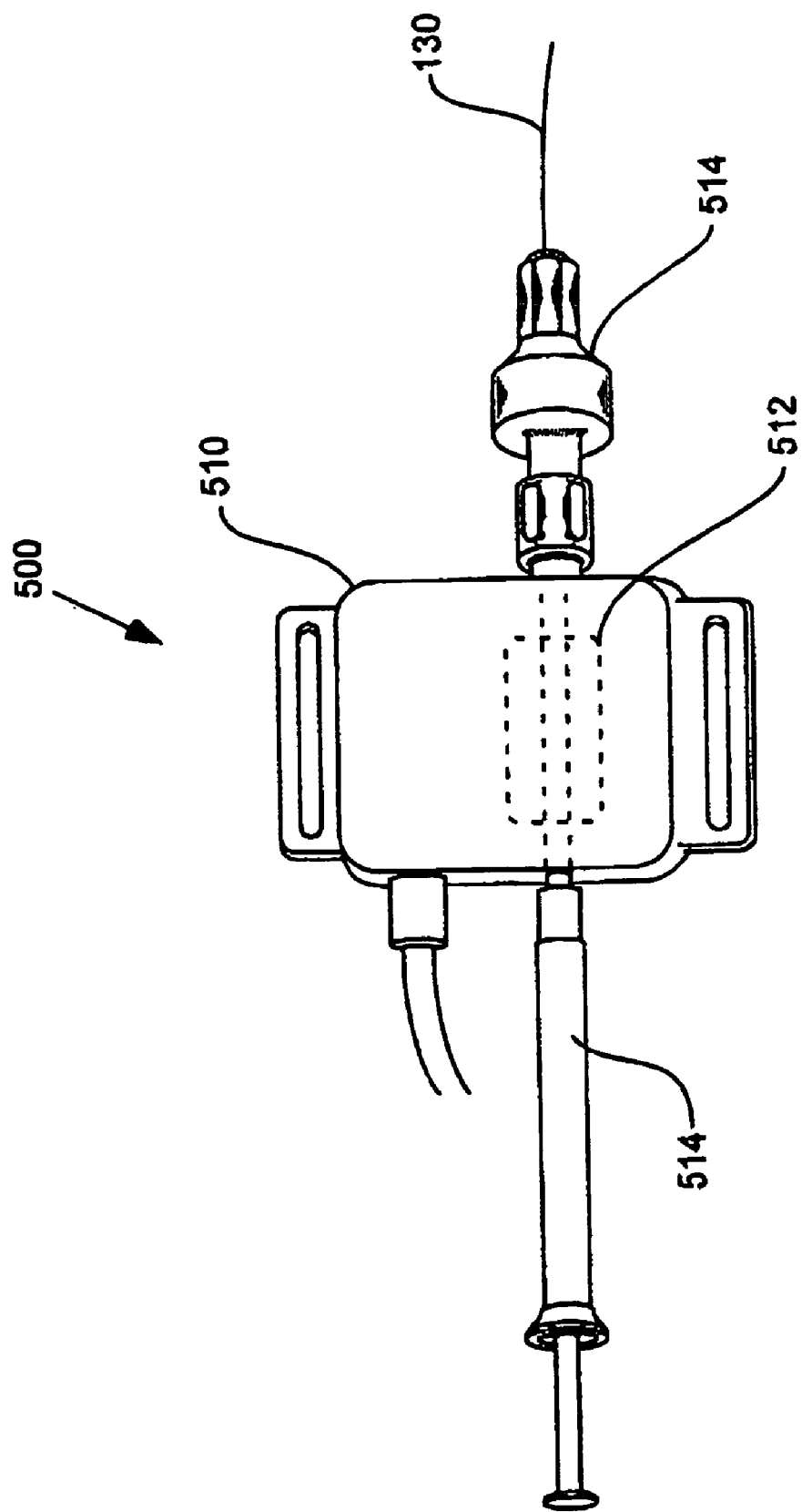
FIG. 5 illustrates a front view of one assembly for measuring the pressure of the fluid in the needle.

FIG. 5 illustrates a front view of one embodiment of a pressure measurement assembly 500 connected to a needle 130. In one embodiment, as shown in FIG. 5, the pressure measurement assembly 500 includes a sensor 512 to measure pressure.

Figure 6:
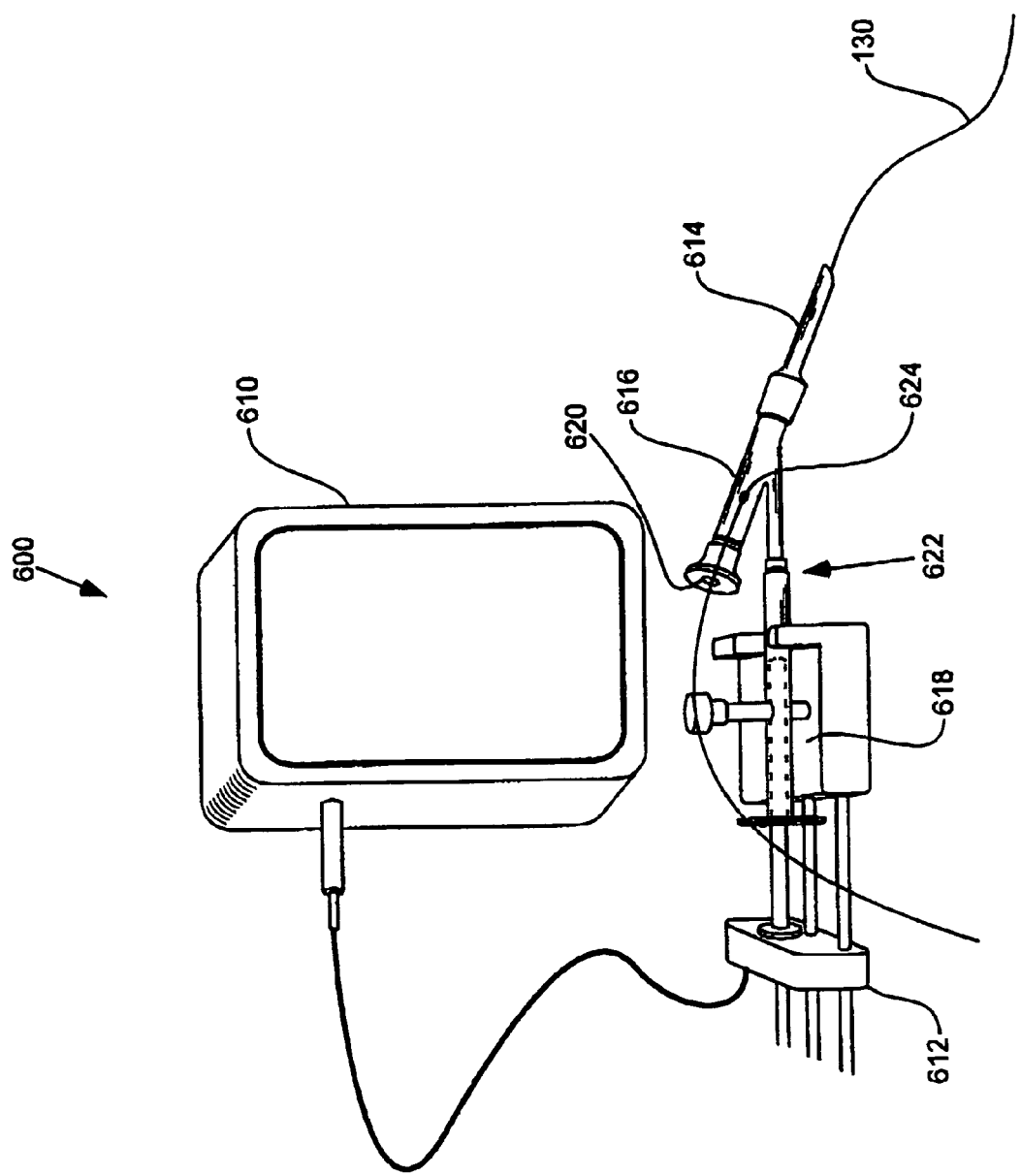
FIG. 6 illustrates a front view of an alternative assembly for measuring the pressure of the fluid in the needle.

As seen in FIG. 5, one end of the pressure measurement assembly 500 is connected to a syringe 514. A syringe pump 612 in FIG. 6 is used to inject the fluid from the syringe 514 and through the needle 130 at a constant, controlled rate. In one embodiment, the sensor 512 detects a first injection pressure increase as the needle tip contacts tissue. The sensor 512 measures a second injection pressure increase as the needle 130 penetrates the tissue to a predetermined depth. The second injection pressure increase occurs as the aperture in the needle (shown in FIGS. 1-3) becomes occluded, thereby increasing the pressure of the therapeutic agent being injected into the tissue.

An example of a pressure measurement assembly 500 that may be utilized with the present invention is a disposable pressure monitoring system manufactured by Utah Medical Products, Inc. The assembly 500 may easily be attached to a luer lock attached to the proximal end of the needle 130. The disposable pressure monitoring system provides fluid path visualization. Different manufacturers may also produce similar pressure measurement systems that are capable of being utilized in the context of the present invention. Alternatively, a much smaller sensor assembly can be integrated directly into the needle assembly. For example, a smaller version of the sensor 512 could be mounted onto a small plastic connector that is used to attach the needle to the syringe.

FIG. 6 illustrates a front view of an alternative embodiment of a pressure measurement assembly 600 connected to the proximal end of the needle 130. The pressure measurement assembly 600 includes a signal processor and pressure display 610. Here, a proximal end of a bifurcated connector 616 has a transducer port 620 and a connection port 622 that connects the bifurcated connector 616 to the syringe 618. The needle 130 is connected to a distal end of the bifurcated connector 616. The syringe 618 is placed on a syringe pump 612.

The syringe pump 612 pumps a therapeutic agent at a constant rate through the needle 130. The therapeutic agent should be pumped very slowly so that the amount of therapeutic agent that is dispensed before the needle reaches the desired penetration depth is minimized. As the needle 130 advances and its tip makes contact with or penetrates tissue, the occlusion of the needle tip creates a first resistance to the flow of the therapeutic agent. This is detected by the pressure sensor 624. Accordingly, the increase in pressure indicates that the needle 130 has contacted tissue.

The operator continues to advance the needle 130 until the tissue begins to occlude the aperture (shown in FIGS. 1-3) of the needle 130. As the aperture becomes fully occluded, this increases the resistance to the flow of the therapeutic agent and results in a second pressure increase as shown in region C in FIG. 4.

Figure 7:
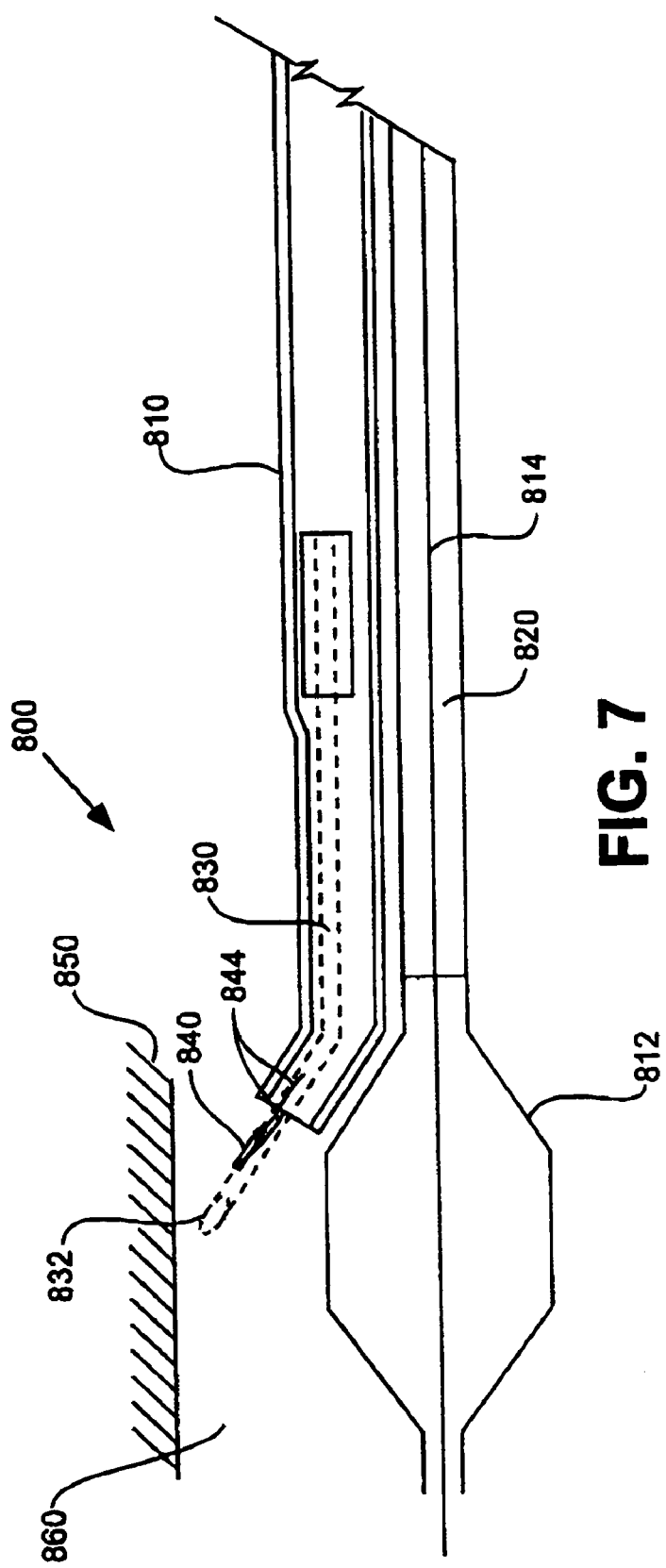
FIG. 7 illustrates a side cross-sectional view of an embodiment of a fluid delivery catheter with a force transducer.

FIG. 7 illustrates a side cross-sectional view of an alternative embodiment of a fluid delivery catheter 800 including an attached strain gauge 840. Similar to FIG. 1, the fluid delivery catheter 800 includes a needle 830 within a needle sheath 810. The needle sheath 810 is attached to a dilatation catheter 820. The dilatation catheter 820 is delivered into the body over a guidewire 814 that guides the dilatation catheter 820 through tortuous pathways within a patient's body to a desired region or body cavity 860. The dilatation catheter 820 may include a balloon 812 that inflates and directs the distal end of the needle sheath 810 and needle 830 toward a vessel wall 850. The operator pushes the needle 830 toward the vessel wall 850 so that a needle tip 832 contacts the vessel wall 850. The needle 830 continues to move into the vessel wall 850 until a predetermined depth is reached. Here, the predetermined depth is reached when the distal portion of the strain gauge 840 contacts the vessel wall 850. As shown in FIG. 7, the strain gauge 840 includes leads 844 extending from the strain gauge 840 to the proximal end of the needle.

An example of a strain gauge 840 that may be utilized with the present invention is a miniature semiconductor strain gauge manufactured by Entran. These strain gauges may be processed from P-type silicon in orientation, which provide maximum sensitivity to applied strain. Different strain gauges may also be available in other configurations. Different manufacturers may also produce similar strain gauges that are capable of being utilized in the present invention. In order to prevent false signals, the signal from the strain gauge should be offset or calibrated to the appropriate level of force that the tissue is expected to exert during successful tissue penetration. The force exerted by the tissue after successful needle penetration is much greater and longer in duration than accidental contact with the needle sheath, catheter assembly or vessel wall. To minimize false signals further, the force measurements should be taken only after the fluid delivery catheter 700 has reached its intended destination.

FIGS. 7a and 7b illustrate the embodiment of the fluid delivery catheter 800 of FIG. 7 in different positions with respect to the vessel wall 850. FIG. 7a illustrates the fluid delivery catheter 800 where the needle 830 has not yet contacted the vessel wall 850. The needle tip 832 is close to and proximate to but not contacting the vessel wall 850.

FIG. 7b illustrates the fluid delivery catheter 800 where a portion of the needle tip 832 is contacting and has become embedded in the vessel wall 850. The needle 830 is inserted a predetermined depth into the vessel wall 850. As seen in FIG. 7, the strain gauge 840 is attached to the needle 830 at a predetermined distance from the needle tip 832. When the needle 830 penetrates the vessel wall 850 a predetermined depth, the strain gauge contacts the vessel wall 850 and senses contact pressure from the tissue. The contact pressure of the tissue thus signals to the operator that a certain penetration depth of the needle 830 has been achieved.

Figure 8:
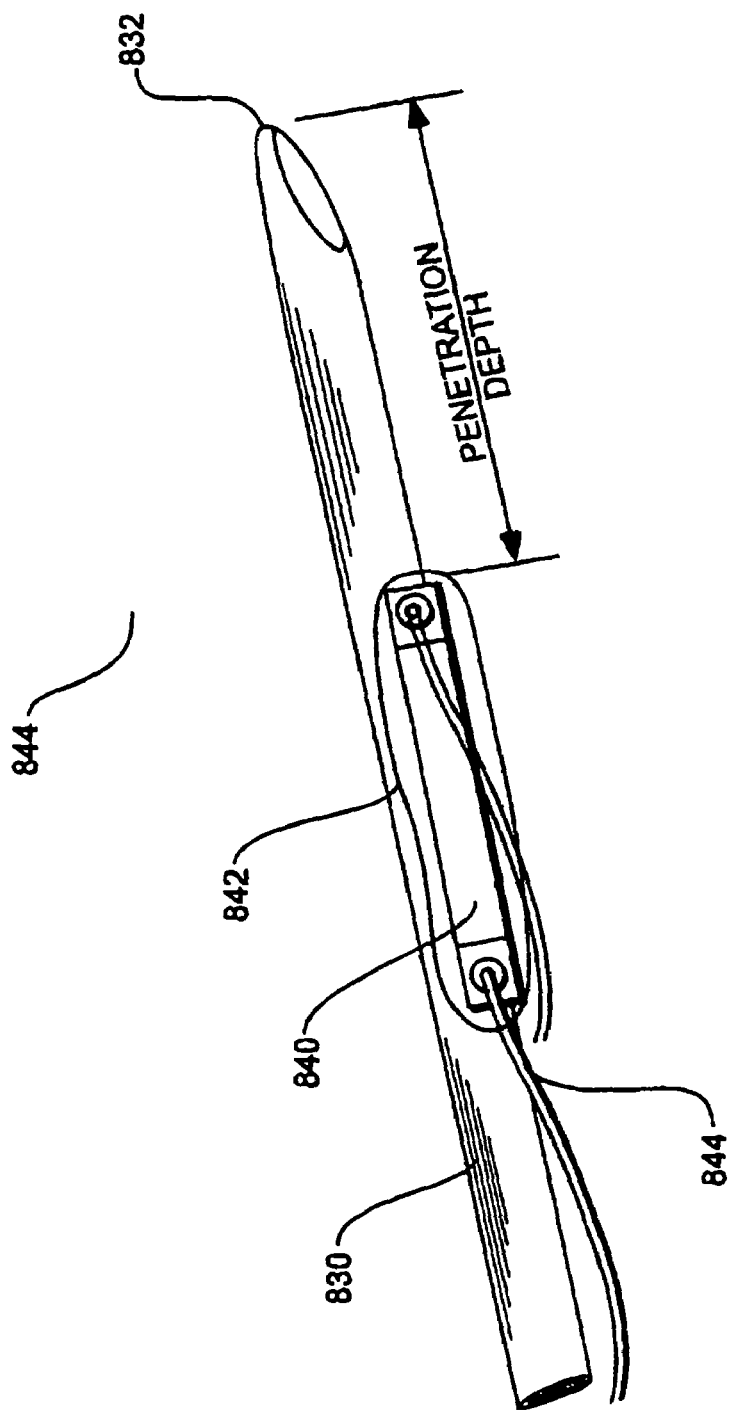
FIG. 8 illustrates an enlarged view of the embodiment of the needle and the force transducer shown in FIG. 7.

FIG. 8 illustrates an enlarged view of the embodiment of the needle 830 and strain gauge 840 shown in FIG. 7. The strain gauge 840 is shown attached to the needle 830 a predetermined distance from the needle tip 832. This allows the needle 830 to be inserted into the vessel wall or tissue to a predetermined penetration depth. In one embodiment, the predetermined depth is 0.5 to 3 millimeters. In one embodiment, as shown in FIG. 8, the strain gauge 840 is covered by an encapsulant 842 to protect the strain gauge 840.

Strain gauges are typically mounted very securely to the item that is expected to deform or experience strain. Since the needle 830 is relatively strong, it will not deform during tissue penetration and the securely mounted strain gauge 840 will not produce a signal. In one embodiment, the strain gauge is embedded in a soft polymeric encapsulant 842 before it is mounted on the needle 830. When the soft encapsulant 842 makes contact with tissue during penetration, it deforms and transfers this energy to the strain gauge 840. In one embodiment, the soft polymeric material encapsulant 842 may be made of silicone. In alternative embodiments, the encapsulant 842 may be made of other biocompatible materials.

Figure 9A:
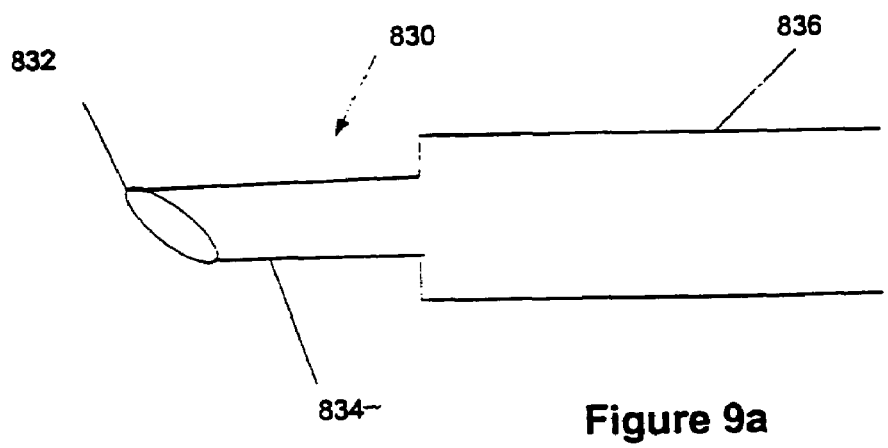
FIG. 9a illustrates an enlarged view of an alternative embodiment of a needle for use in the fluid delivery catheter shown in FIG. 7.

FIG. 9a illustrates an enlarged view of an alternative embodiment of a needle 830 used in the fluid delivery catheter shown in FIG. 7. Here, the needle 830 has a stepped design with a distal (first) portion 834 and a proximal (second) portion 836. The needle tip is 832 is located on the distal portion 834. The distal portion 834 has a smaller diameter than the proximal portion 836. In one embodiment, the distal portion 832 has an outer diameter of 0.008 to 0.26 inches.

Figure 9B:
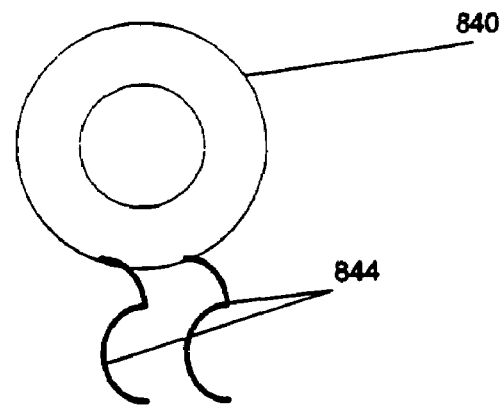
FIG. 9b illustrates an enlarged view of an alternative embodiment of a force transducer for use in the fluid delivery catheter shown in FIG. 7.
Figure 9C:
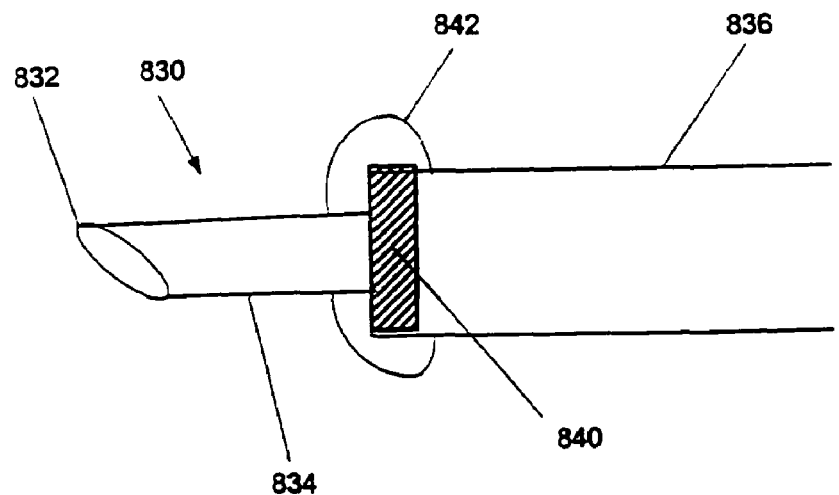
FIG. 9c illustrates an enlarged view of the needle of FIG. 9a and the force transducer of FIG. 9b.

FIG. 9b illustrates an enlarged view of an alternative embodiment of a piezoelectric transducer 840 for use in the fluid delivery catheter as shown in FIG. 7. The piezoelectric transducer 840 is shown with leads 844. This piezoelectric transducer 840 is also seen in conjunction with the needle 830 in FIG. 9c. As seen in FIG. 9c, the piezoelectric transducer 840 is located on the stepped portion of the needle between distal portion 834 and the proximal portion 836 of the needle 830. The encapsulant 842 is located around the piezoelectric transducer 840. The stepped needle design is not necessary but may help to support the piezoelectric transducer 840 and improve manufacturability.

In one embodiment, the distal portion 834 of the needle 830 may have an outer diameter of 0.008 to 0.26 inches and a proximal portion diameter of 0.012 to 0.3 inches. In alternative embodiments, these dimensions may change according to application.

Figure 10:
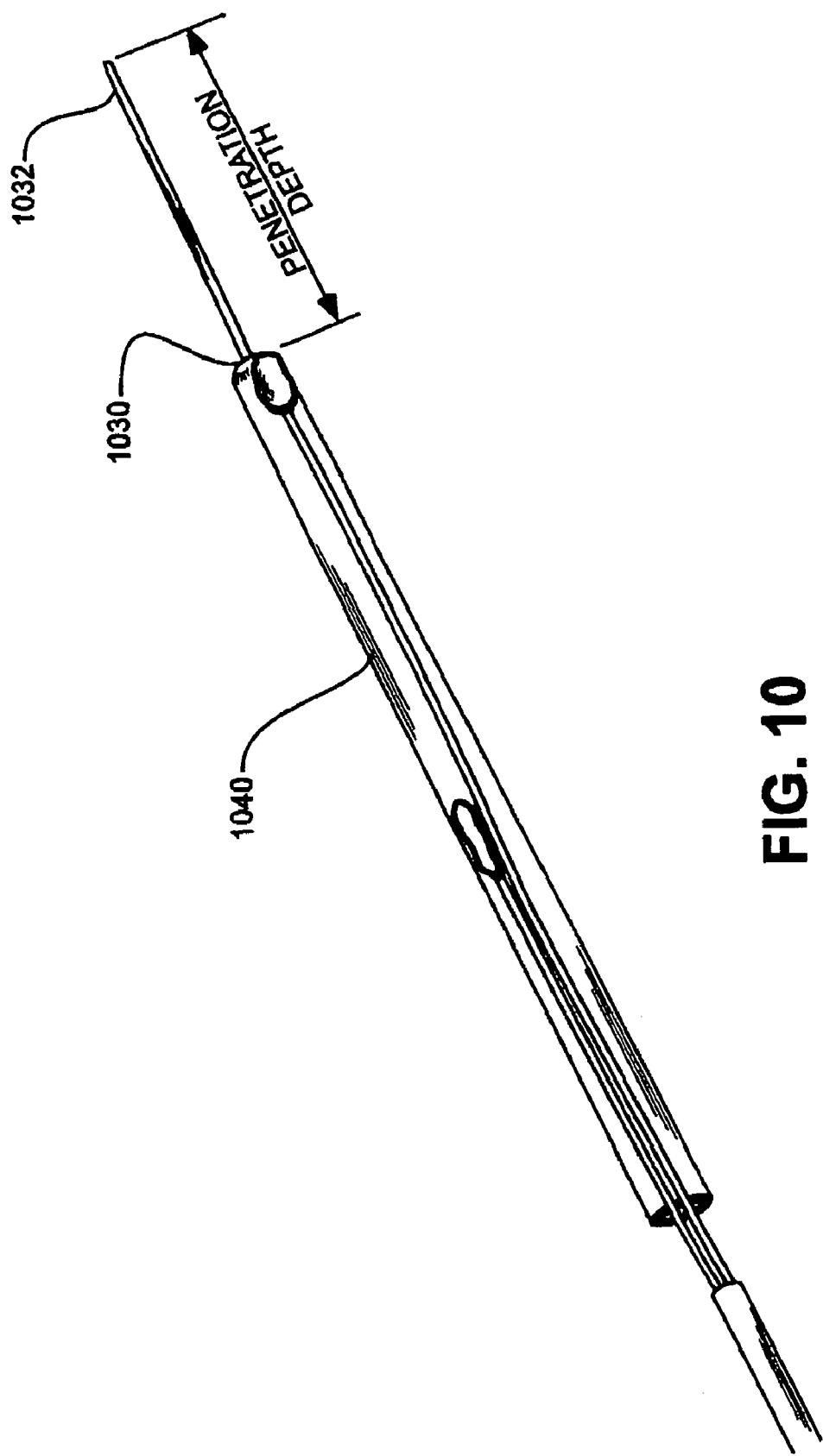
FIG. 10 illustrates a front view of one embodiment of a piezoelectric force transducer connected to the second end of a needle.

FIG. 10 illustrates a side view of one embodiment of a piezoelectric transducer with a tubular shape 1040 connected to the needle 1030. The piezoelectric transducer 1040 is located a predetermined distance from the needle tip 1032 so that an operator may detect when the needle 1030 has reached the desired penetration depth in the tissue.

In one embodiment the piezoelectric transducer 1040 may also be covered by a soft encapsulant material as was shown for the strain gauge discussed above in reference to FIGS. 7-9. In an alternative embodiment, the piezoelectric transducer may not be covered by the encapsulant material.

Figure 11:
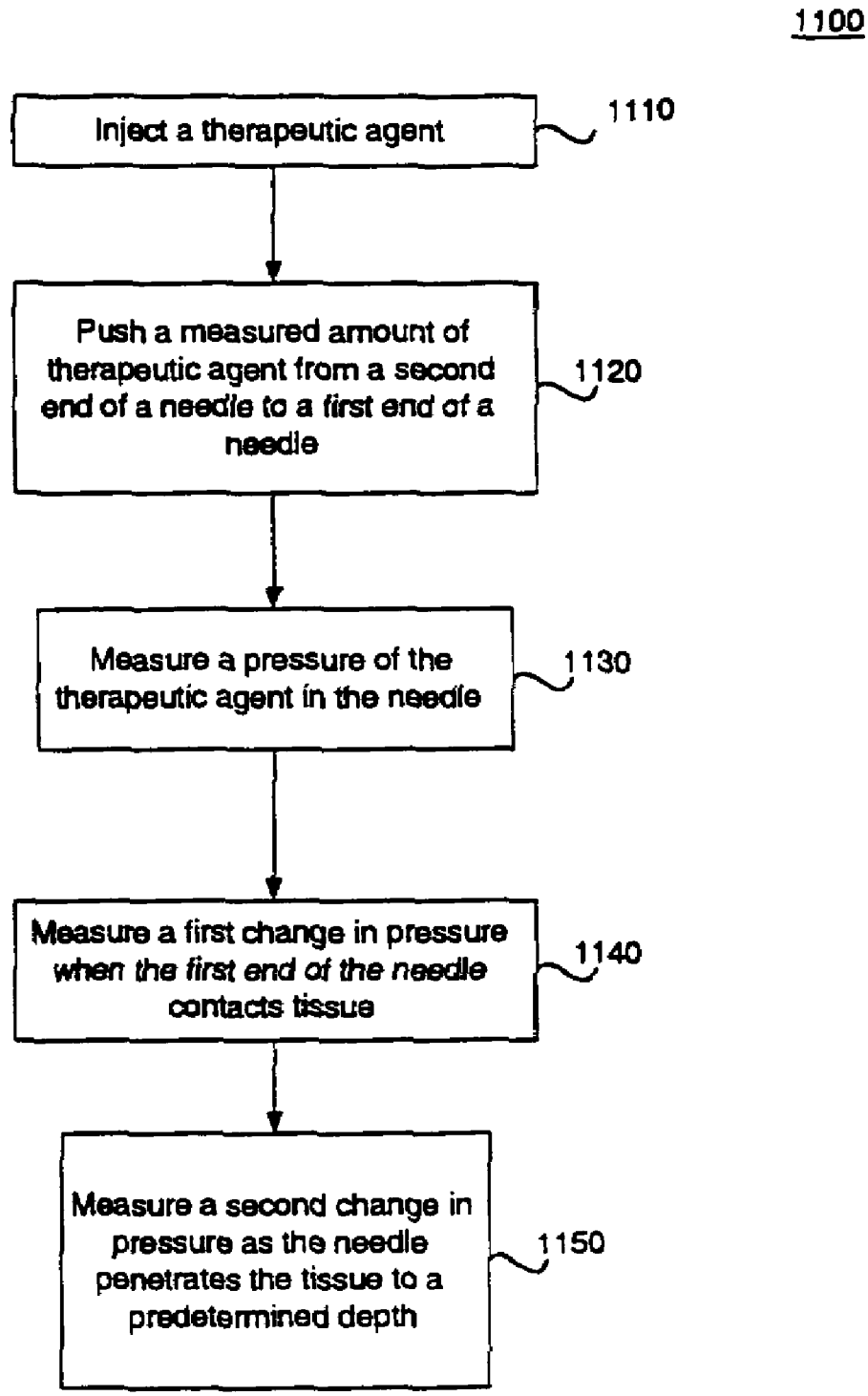
FIG. 11 illustrates a flow diagram of one embodiment of a process for detecting tissue contact and needle penetration depth.

FIG. 11 illustrates the flow chart of one embodiment of a process 1100 of detecting tissue contact and needle penetration depth. At processing block 1110 the syringe dispenses a therapeutic agent through the needle.

At processing block 1120, the needle dispenses a measured amount of therapeutic agent from a second end of a needle to a first end of the needle. At processing block 1130, the pressure of the therapeutic agent in the needle is measured. At processing block 1140, a first increase in pressure is measured when the first end of the needle contacts tissue. At processing block 1150, a second increase in pressure is measured as the needle penetrates into the tissue to a predetermined depth.

Systems and methods for detecting tissue contact and needle penetration depth have been described. Although the present invention has been described with reference to specific exemplary embodiments, it will be evident that various modifications and changes may be made to these embodiments without departing from the broader spirit and scope of the invention. Accordingly, the specification and drawings are to be regarded in an illustrative rather than a restrictive sense.

What is claimed is:

1. A method of detecting tissue contact and a needle penetration depth of a needle used internally to deliver a therapeutic agent to a patient comprising:
   dispensing a measured amount of therapeutic agent through a lumen of a needle and from a second end of the needle to a first end of the needle at a predetermined flow rate, wherein the second end of the needle is connected to a pressure measurement assembly;
   measuring a pressure of the therapeutic agent in the needle wherein measuring the pressure includes;
   measuring a first change in pressure by measuring a change in the flow rate of the therapeutic agent dispensed through the lumen of the needle when the first end of the needle contacts a tissue and the first end of the needle becomes occluded; and
   measuring a second change in pressure when the needle penetrates the tissue further and when a first aperture located a predetermined distance from the first end of the needle becomes occluded by measuring another change in the flow rate of the therapeutic agent dispensed through the lumen of the needle, wherein said predetermined distance is used to specify a depth of the needle.

2. The method of claim 1 wherein measuring pressure of the therapeutic agent in the needle includes measuring pressure of the therapeutic agent using a pressure measurement assembly.

3. The method of claim 1 wherein the therapeutic agent is one of a drug, growth factor, and gene therapy.

4. The method of claim 1 wherein the predetermined depth ranges between 0.5 and 10 millimeters.

* * * * *